US012614633B2

(12) United States Patent
Teplitzky

(10) Patent No.: US 12,614,633 B2
(45) Date of Patent: Apr. 28, 2026

(54) ELECTROCARDIOGRAM WAVE SEGMENTATION USING MACHINE LEARNING

(71) Applicant: Preventice Solutions, Inc., Rochester, MN (US)

(72) Inventor: Benjamin A. Teplitzky, Rochester, MN (US)

(73) Assignee: Preventice Solutions, Inc., Rochester, MN (US)

( * ) Notice: Subject to any disclaimer, the term of this patent is extended or adjusted under 35 U.S.C. 154(b) by 599 days.

(21) Appl. No.: 17/973,739

(22) Filed: Oct. 26, 2022

(65) Prior Publication Data

US 2023/0137626 A1 May 4, 2023

Related U.S. Application Data

(60) Provisional application No. 63/272,961, filed on Oct. 28, 2021.

(51) Int. Cl.
| | |
|---|---|
| *A61B 5/346* | (2021.01) |
| *A61B 5/00* | (2006.01) |
| *A61B 5/349* | (2021.01) |
| *G16H 40/63* | (2018.01) |

(52) U.S. Cl.
CPC ............. *G16H 40/63* (2018.01); *A61B 5/349* (2021.01); *A61B 5/7203* (2013.01)

(58) Field of Classification Search
CPC ...... A61B 5/349; A61B 5/7203; A61B 5/7264
See application file for complete search history.

(56) References Cited

U.S. PATENT DOCUMENTS

| | | | | |
|---|---|---|---|---|
| 3,927,663 A | * | 12/1975 | Russell | A61B 5/352 |
| | | | | 128/901 |
| 6,263,238 B1 | * | 7/2001 | Brewer | A61N 1/3925 |
| | | | | 607/5 |
| 12,268,527 B2 | * | 4/2025 | Kalidas | A61B 5/364 |
| 2009/0069703 A1 | * | 3/2009 | Takla | A61B 5/318 |
| | | | | 600/509 |
| 2009/0069709 A1 | | 3/2009 | Takla | |
| 2014/0187988 A1 | | 7/2014 | Ong et al. | |
| 2018/0368723 A1 | * | 12/2018 | Ibáñez Català | A61B 5/361 |
| 2019/0216350 A1 | | 7/2019 | Sullivan et al. | |
| 2019/0354787 A1 | * | 11/2019 | Fong | G06V 10/454 |
| 2020/0305799 A1 | | 10/2020 | Cao et al. | |

(Continued)

OTHER PUBLICATIONS

International Search Report and Written Opinion received for PCT Patent Application No. PCT/US2022/047809, mailed on Jan. 27, 2023, 11 pages.

(Continued)

*Primary Examiner* — Eric D. Bertram
(74) *Attorney, Agent, or Firm* — Faegre Drinker Biddle & Reath, LLP

(57) ABSTRACT

A method includes classifying, using a machine learning model, a portion of an electrocardiogram measurement as an artifact. The method further includes normalizing the electrocardiogram measurement except the portion of the electrocardiogram measurement classified as the artifact. The method further includes applying the machine learning model to the normalized electrocardiogram measurement to detect a cardiac event.

2 Claims, 6 Drawing Sheets

(56) References Cited

U.S. PATENT DOCUMENTS

| | | | | |
|---|---|---|---|---|
| 2020/0349247 | A1* | 11/2020 | Seo | A61B 5/36 |
| 2020/0352462 | A1* | 11/2020 | Pedalty | A61B 5/363 |
| 2020/0357517 | A1 | 11/2020 | Haddad et al. | |
| 2020/0357519 | A1* | 11/2020 | Chakravarthy | G16H 40/67 |
| 2022/0015711 | A1* | 1/2022 | Kalidas | G06N 20/20 |
| 2023/0282352 | A1* | 9/2023 | Kim | G06Q 50/22 |
| | | | | 705/2 |

OTHER PUBLICATIONS

Zhang et al., "A novel machine learning-enabled framework for instantaneous heart rate monitoring from motion-artifact-corrupted electrocardiogram signals," Physiological Measurement, vol. 37, No. 11, Sep. 28, 2011, pp. 1945-1967.

International Search Report and Written Opinion for International patent application No. PCT/US2022/047809, filed Oct. 26, 2022, mailed Feb. 8, 2023.

Qingxue Zhang et al. "A novel machine learning-enabled framework for instantaneous heart rate monitoring from motion artifact corrupted electrocardiogram signals," Physiological Measurement, Institute of Physics Publishing Bristol, GB, vol. 37, No. 11, Sep. 28, 2016, pp. 1945-1967, XP020310127, ISSN: 0967-3334, DOI: 10.1088/0967-3334/37/111945 [retrieved on Sep. 28, 2016] abstract.

\* cited by examiner

116

114

<u>106</u>

118

NORMALIZED ECG MEASUREMENTS → MACHINE LEARNING MODEL → CARDIAC EVENT

<u>106</u>

602

LABELED ECG MEASUREMENTS

602

LABELED ECG MEASUREMENTS

602

LABELED ECG MEASUREMENTS

114

MACHINE LEARNING MODEL

ELECTROCARDIOGRAM WAVE SEGMENTATION USING MACHINE LEARNING

CROSS-REFERENCE TO RELATED APPLICATION

This application claims priority to Provisional Application No. 63/272,961, filed Oct. 28, 2021, which is herein incorporated by reference in its entirety.

BACKGROUND

Electrocardiograms (ECGs) use electrodes positioned on a patient's body to detect the patient's heartbeat. The measurements from an ECG are typically displayed as a wave signal, with the heartbeat represented by crests and troughs in the wave. Different cardiac events and conditions can be detected by monitoring various characteristics of the wave signal (e.g., characteristics of the p-wave, QRS complex, and t-wave generated by an individual heartbeat).

Machine learning models have been applied to ECG wave signals to detect cardiac events. One technique for training or applying the machine learning models involves normalizing the wave signals, which improves convergence. Normalizing ECG wave signals, however, is complex and challenging because different wave signals can originate from different ECG devices with different voltage ranges, gains, and/or filters. Even if wave signals originate from the same ECG device, degradations in the ECG sensor connected to a patient may cause measured wave signals to change over time. Additionally, different ECG wave signals may be generated in different environments with different levels of noise or disturbance that affect the wave signals. For example, some ECG wave signals may include voltage spikes that were not generated by a heartbeat but negatively impact and degrade the normalization. As another example, some disturbances may cause an ECG wave signal to attenuate at the voltage supply rail (which may be referred to as "railing"). When the wave signal is filtered, the attenuated section of the wave signal may be completely removed, which causes that section to resemble a stopped heartbeat (which may be referred to as a "false pause").

OVERVIEW

According to one example ("Example 1"), a method that includes dividing electrocardiogram measurements of a patient into a plurality of segments; classifying, using a machine learning model, a first segment of the plurality of segments as an artifact; normalizing the electrocardiogram measurements corresponding to the plurality of segments except the electrocardiogram measurements corresponding to the first segment to produce normalized electrocardiogram measurements; and applying the machine learning model to the normalized electrocardiogram measurements to detect a cardiac event in the patient.

According to another example ("Example 2") further to the method of Example 1, the first segment is classified as the artifact based on a voltage spike in the first segment.

According to another example ("Example 3") further to the method of any one of Examples 1-2, classifying the first segment as the artifact includes classifying, using the machine learning model, the first segment as a pause indicating that a heart of the patient stopped; determining a probability that classifying the first segment as the pause is correct; and classifying the first segment as the artifact in response to determining that the probability does not meet a threshold.

According to another example ("Example 4") further to the method of any one of Examples 1-3, the method may also include training the machine learning model using labeled electrocardiogram measurements, wherein the labeled electrocardiogram measurements comprise labeled segments, and wherein the labeled segments comprise a segment labeled as an artifact.

According to another example ("Example 5") further to the method of any one of Examples 1-4, normalizing the electrocardiogram measurements comprises changing voltage levels of the electrocardiogram measurements such that an average voltage level of the electrocardiogram measurements is zero and such that a standard deviation of the electrocardiogram measurements is one.

According to another example ("Example 6") further to the method of any one of Examples 1-5, classifying the first segment as the artifact also includes determining a probability that classifying the first segment as the artifact is correct; and classifying the first segment as the artifact in response to determining that the probability meets a threshold.

According to another example ("Example 7") further to the method of any one of Examples 1-6, each of the plurality of segments have a same duration. According to one example ("Example 8"), an apparatus includes a memory; and a hardware processor communicatively coupled to the memory, the hardware processor configured to: divide electrocardiogram measurements of a patient into a plurality of segments, classify, using a machine learning model, a first segment of the plurality of segments as an artifact, normalize the electrocardiogram measurements corresponding to the plurality of segments except the electrocardiogram measurements corresponding to the first segment to produce normalized electrocardiogram measurements; and apply the machine learning model to the normalized electrocardiogram measurements to detect a cardiac event in the patient.

According to another example ("Example 9"), further to the apparatus of Example 8, the first segment is classified as the artifact based on a voltage spike in the first segment.

According to another example ("Example 10"), further to the apparatus of any one of Examples 8-9, classifying the first segment as the artifact includes classifying, using the machine learning model, the first segment as a pause indicating that a heart of the patient stopped; determining a probability that classifying the first segment as the pause is correct; and classifying the first segment as the artifact in response to determining that the probability does not meet a threshold.

According to another example ("Example 11"), further to the apparatus of any one of Examples 8-10, the hardware processor further configured to train the machine learning model using labeled electrocardiogram measurements, wherein the labeled electrocardiogram measurements comprise labeled segments, and wherein the labeled segments comprise a segment labeled as an artifact.

According to another example ("Example 12"), further to the apparatus of any one of Examples 8-11, normalizing the electrocardiogram measurements comprises changing voltage levels of the electrocardiogram measurements such that an average voltage level of the electrocardiogram measurements is zero and such that a standard deviation of the electrocardiogram measurements is one.

According to another example ("Example 13"), further to the apparatus of any one of Examples 8-12, wherein classifying the first segment as the artifact also includes determining a probability that classifying the first segment as the artifact is correct; and classifying the first segment as the artifact in response to determining that the probability meets a threshold.

According to another example ("Example 14"), further to the apparatus of any one of Examples 8-13, each of the plurality of segments have a same duration.

According to one example ("Example 15") a method includes classifying, using a machine learning model, a portion of an electrocardiogram measurement as an artifact; normalizing the electrocardiogram measurement except the portion of the electrocardiogram measurement classified as the artifact; and applying the machine learning model to the normalized electrocardiogram measurement to detect a cardiac event.

According to another example ("Example 16"), further to the method of Example 15, the portion is classified as the artifact based on a voltage spike in the portion.

According to another example ("Example 17"), further to the method of any one of Examples 15-16, classifying the portion as the artifact includes classifying, using the machine learning model, the portion as a pause indicating that a heart stopped; determining a probability that classifying the portion as the pause is correct; and classifying the portion as the artifact in response to determining that the probability does not meet a threshold.

According to another example ("Example 18"), further to the method of any one of Examples 15-17, the method also includes training the machine learning model using labeled electrocardiogram measurements, wherein the labeled electrocardiogram measurements comprise labeled segments, and wherein the labeled segments comprise a segment labeled as an artifact.

According to another example ("Example 19"), further to the method of any one of Examples 15-18, normalizing the electrocardiogram measurement comprises changing voltage levels of the electrocardiogram measurement such that an average voltage level of the electrocardiogram measurement is zero and such that a standard deviation of the electrocardiogram measurement is one.

According to another example ("Example 20"), further to the method of any one of Examples 15-19, classifying the portion as the artifact also includes determining a probability that classifying the portion as the artifact is correct; and classifying the portion as the artifact in response to determining that the probability meets a threshold.

This Overview is an overview of some of the teachings of the present application and is not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Various aspects of the present disclosure are directed toward computing systems and methods that use machine learning to normalize electrocardiogram (ECG) wave signals. The computing system may apply a deep neural network to an ECG wave signal to label portions of the ECG wave signal as "clean" (indicating that the portion represents a heartbeat), "artifact" (indicating that the portion does not represent a heartbeat), or "pause" (indicating that the portion represents a stopped heartbeat). The computing system may then normalize the ECG wave signal but excludes the portions labeled "artifact" from the normalization. As a result, the normalization is not performed on artifacts (e.g., voltage spikes and false pauses) that negatively impact or degrade the normalization. The computing system applies the machine learning model to the normalized ECG wave signal to detect cardiac events. In certain embodiments, the normalized ECG wave signal produces a more accurate detection or prediction of cardiac events compared to prior systems, which improves the health of a patient. For example, some previous systems could not identify and exclude voltage spikes and false pauses in ECG wave signals. As a result, when the previous systems normalized the ECG wave signals, the voltage spikes and false pauses would distort the normalization (e.g., cause portions of the ECG wave signals generated by a heartbeat to appear smaller in magnitude or shorter in duration or cause the voltage spike or false pauses to appear legitimate). When a human monitor or computing system reviewed the normalized ECG wave signals, the distortions in the normalized ECG wave signals may cause the human monitor or computing system to reach incorrect diagnoses, leading to incorrect treatment. By contrast, the disclosed computing system may apply machine learning to identify and exclude artifacts, such as voltage spikes and false pauses, from normalization, which may prevent the distortions in the normalized ECG wave signals. As a result, the human monitor or computing system that analyzes the normalized ECG wave signals may make correct diagnoses, leading to correct treatment.

Figure 1:
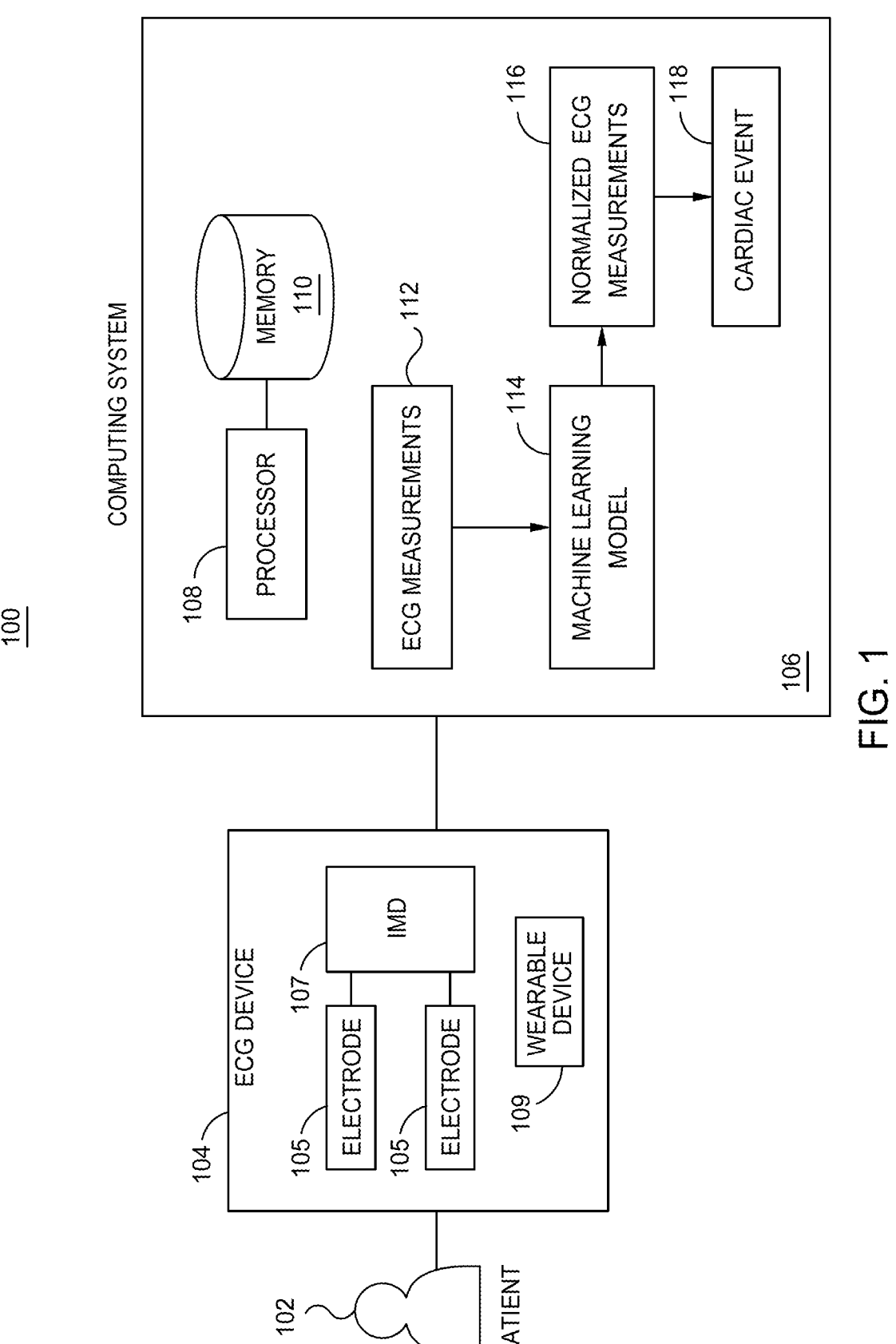
FIG. 1 illustrates an example system, in accordance with various aspects of the present disclosure.

FIG. 1 illustrates an example system 100, in accordance with various aspects of the present disclosure. As seen in FIG. 1, the system 100 includes an ECG device 104 and a computing system 106. The computing system 106 applies one or more machine learning models to measurements from the ECG device 104 to identify artifacts in the measurements that were likely not generated by a heartbeat. The computing system 106 then excludes the artifacts when normalizing the ECG measurements. The computing system 106 analyzes the normalized ECG measurements to determine or predict a cardiac event. In particular embodiments, analyzing the normalized ECG measurements provides a more accurate detection or prediction of cardiac events, which improves patient health.

The ECG device 104 may be connected, placed, attached to or implanted in the patient 102 to detect a heartbeat in the patient 102. The ECG device 104 may include one or more electrodes 105 that adhere or attach to the body of the patient 102. In other instances, the ECG device 104 may include one or more electrodes 105 arranged with, for example, an implantable medical device (IMD) 107 subcutaneously implanted in a chest, abdomen, or other parts of the patient 102. Examples of the IMD 107 may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The ECG device 104 alternatively or additionally may include a subcutaneous medical device such as a subcutaneous monitor or diagnostic device, external monitoring or therapeutic medical devices such as automatic external defibrillators (AEDs) or Holter monitors, or wearable medical devices 109 such as patch-based devices, smart watches, or smart accessories.

The ECG device 104 may include one or more wearable devices 109 (e.g., smartwatch), a portable computing device (e.g., smartphone), a medical device (e.g., a wearable medical device (WMD)), and/or the like. For example, the ECG device 104 may include a control device, a monitoring device, a respiratory device, a pacemaker, a cardiac resynchronization therapy (CRT) device and/or the like, and may be a wearable device and/or medical device known in the art or later developed, for sensing physiological parameters of the patient 102, providing therapy and/or diagnostic data about the patient 102 and/or the ECG device 104. In various embodiments, the ECG device 104 may include inhaler functionality, nebulizer functionality, ventilating functionality, defibrillation, and pacing/CRT capabilities (e.g., a CRT-D device). In embodiments, the ECG device 104 may be wearable on the patient 102 and may be configured to monitor (e.g., sense and/or record) physiological parameters associated with patient 102 (e.g., respiratory system, and/or circulatory system). In embodiments, the ECG device 104 may be configured to record physiological parameters such as, for example, one or more respiratory signals, cardiac electrical signals, spirometry, oximetry, arterial blood gas measurements, heart sounds, heart rate, blood pressure measurements, oxygen saturations, and/or the like.

The ECG device 104 may include any type of medical device (e.g., a wearable medical device (WMD) 109, an implantable medical device (IMD) 107, etc.) that senses one or more physiological signals of the patient 102, administers one or more therapies, and/or the like, and may include any number of different components of a medical device. For example, the ECG device 104 may include a control device, a monitoring device, a respiratory device, a pacemaker, an implantable cardioverter defibrillator (ICD), a cardiac resynchronization therapy (CRT) device, a neurostimulation device, a drug delivery device, a muscular stimulation device, an optimal or audio stimulation device, and/or the like, and may be a medical device known in the art or later developed, for sensing physiological signals, providing therapy and/or diagnostic data about the patient and/or the ECG device 104. In various embodiments, the ECG device 104 may include a drug delivery functionality (e.g., an inhaler functionality, a nebulizer functionality and/or the like), ventilating functionality, defibrillation, an air filtration functionality, a smoking cessation functionality, an oxygen delivery functionality, a volatile compound release functionality, and/or pacing/CRT capabilities (e.g., a CRT-D device). In embodiments, the ECG device 104 may be implanted subcutaneously within an implantation location or pocket in the patient's 102 chest or abdomen and may be configured to monitor (e.g., sense and/or record) physiological parameters associated with one or more body systems of the patient 102 (e.g., the respiratory system, the nervous system, and/or the circulatory system). In embodiments, the ECG device 104 may be an implantable respiratory monitor, an implantable cardiac monitor (ICM) (e.g., an implantable diagnostic monitor (IDM), an implantable loop recorder (ILR), etc.) configured to record physiological parameters such as, for example, one or more respiratory signals, cardiac electrical signals, spirometry, oximetry, arterial blood gas measurements, heart sounds, heart rate, blood pressure measurements, oxygen saturations, and/or the like.

The computing system 106 analyzes measured data from the ECG device 104 to determine whether a cardiac event is occurring in the patient 102. Generally, the computing system 106 applies one or more machine learning models to the data from the ECG device 104 to identify artifacts in that data, which are likely not generated by a heartbeat. The computing system 106 then normalizes the data from the ECG device 104 but excludes the artifacts from the normalization. The computing system 106 analyzes the normalized ECG data to determine or predict cardiac events in the patient 102. As seen in FIG. 1, the computing system 106 includes a processor 108 and a memory 110 that perform the actions or functions of the computing system 106 described herein.

The processor 108 is any electronic circuitry, including, but not limited to one or a combination of microprocessors, microcontrollers, application specific integrated circuits (ASIC), application specific instruction set processor (ASIP), and/or state machines, that communicatively couples to memory 110 and controls the operation of the computing system 106. The processor 108 may be 8-bit, 16-bit, 32-bit, 64-bit or of any other suitable architecture. The processor 108 may include an arithmetic logic unit (ALU) for performing arithmetic and logic operations, processor registers that supply operands to the ALU and store the results of ALU operations, and a control unit that fetches instructions from memory and executes them by directing the coordinated operations of the ALU, registers and other components. The processor 108 may include other hardware that operates software to control and process information. The processor 108 executes software stored on the memory 110 to perform any of the functions described herein. The processor 108 controls the operation and administration of the computing system 106 by processing information (e.g., information received from the ECG device 104 and the memory 110). The processor 108 is not limited to a single processing device and may encompass multiple processing devices.

The memory 110 may store, either permanently or temporarily, data, operational software, or other information for the processor 108. The memory 110 may include any one or a combination of volatile or non-volatile local or remote devices suitable for storing information. For example, the memory 110 may include random access memory (RAM), read only memory (ROM), magnetic storage devices, optical storage devices, or any other suitable information storage device or a combination of these devices. The software represents any suitable set of instructions, logic, or code embodied in a computer-readable storage medium. For example, the software may be embodied in the memory 110, a disk, a CD, or a flash drive. In particular embodiments, the software may include an application executable by the processor 108 to perform one or more of the functions described herein.

The computing system 106 receives ECG measurements 112 from the ECG device 104. The ECG measurements 112 include an electric signal representing the heartbeat of the patient 102. A voltage of the electric signal changes according to the patient's 102 heartbeat. For example, as the patient's 102 heart constricts and expands the voltage of the electric signal changes to represent the beating of the heart. Because the ECG measurements 112 use an electric voltage to represent the heartbeat of the patient 102, different factors may distort the electric signal and make it more difficult to analyze the ECG measurements 112. For example, environmental factors (e.g., movement of the patient 102 or the ECG device 104) may add noise to the ECG measurements 112 or cause voltage spikes in the ECG measurements 112. In some instances, these voltage spikes may attenuate at the voltage supply rail of the ECG device 104. When the electric signal is filtered, the attenuated portions of the electric signal may be removed, which produces a signal that resembles a stopped heartbeat. This phenomenon may be referred to as a "false pause." The voltage spikes and false pauses in the ECG measurements 112 may make it difficult for the computing system 106 to normalize the ECG measurements 112.

The computing system 106 applies one or more machine learning models 114 to the ECG measurements 112 to classify portions of the electric signal in the ECG measurements 112. In some embodiments, the one or more machine learning models 114 include a deep neural network. The deep neural network includes a feature extraction component, a memory component, and a prediction component. The feature extraction component may contain convolutional layers or fully connected layers and may include or exclude other commonly used layers and connections such as batch normalization, dropout, pooling, a non-linear activation function, residual connections, and additional fully connected layers. The memory component may be a bidirectional long short-term memory (LSTM) circuit or any other type of recurrent neural network, such as a unidirectional LSTM circuit or a gated recurrent unit. The prediction component is a fully connected layer and may include a softmax activation function, which produces probabilities for each possible classification.

In some embodiments, the computing system 106 divides the ECG measurements 112 into multiple segments. The computing system 106 then applies the one or more machine learning models 114 to each segment to classify the segment as "clean," "artifact," or "pause." The clean classification indicates that the segment was likely generated by a heartbeat. The artifact classification indicates that the segment was likely not generated by a heartbeat. The pause classification indicates that the segment represents a stopped heartbeat. The one or more machine learning models 114 may also provide probabilities that the classification for a segment is correct. The computing system 106 may classify the segments of the ECG measurements 112 that include voltage spikes or false pauses as artifacts, because the voltage spikes or false pauses are not generated by a heartbeat. The computing system 106 is not limited to classifying the segments of the ECG measurements as clean, artifact, or pause. The computing system 106 may apply any suitable number of classifications to the segments of the ECG measurements 112.

After the segments are classified, the computing system 106 normalizes the ECG measurements 112 to produce normalized ECG measurements 116. The computing system 106 excludes the segments of the ECG measurements 112 that are classified as artifacts from the normalization process. As a result, the computing system 106 does not include the artifacts in the normalization. During normalization, the computing system 106 may scale the segments of the ECG measurements 112 that are not classified as artifacts such that the scaled segments have a certain average voltage (e.g., zero volts) and/or a certain standard deviation (e.g., one volt). By removing artifacts such as voltage spikes and false pauses from the normalization, the computing system 106 prevents the artifacts from distorting the normalization. The normalized ECG measurements 116 that result from scaling the ECG measurements 112 improve convergence and lead to more accurate predictions of cardiac events, in particular embodiments. Additionally, through normalization, the computing system 106 can accurately analyze ECG measurements 112 from different ECG devices 104 that may have different voltage ranges, gains, or filters.

The computing system 106 applies one or more machine learning models 114 to the normalized ECG measurements 116 to detect whether a cardiac event 118 is occurring in the patient 102. The one or more machine learning models 114 may analyze different characteristics of the normalized ECG measurements 116 (e.g., the shape of the electric signal in the normalized ECG measurements 116, the time between heartbeats in the normalized ECG measurements 116, or the occurrence of pauses in the normalized ECG measurements 116) to determine whether a cardiac event 118 is occurring in the patient 102. If a cardiac event 118 is detected, the computing system 106 may generate or communicate to a monitor or administrator an alert indicating that the cardiac event 118 is occurring in the patient 102. The monitor or administrator diagnoses the cardiac event 118 and prescribes proper treatment for the patient 102, which improves the health of the patient 102.

Figure 2:
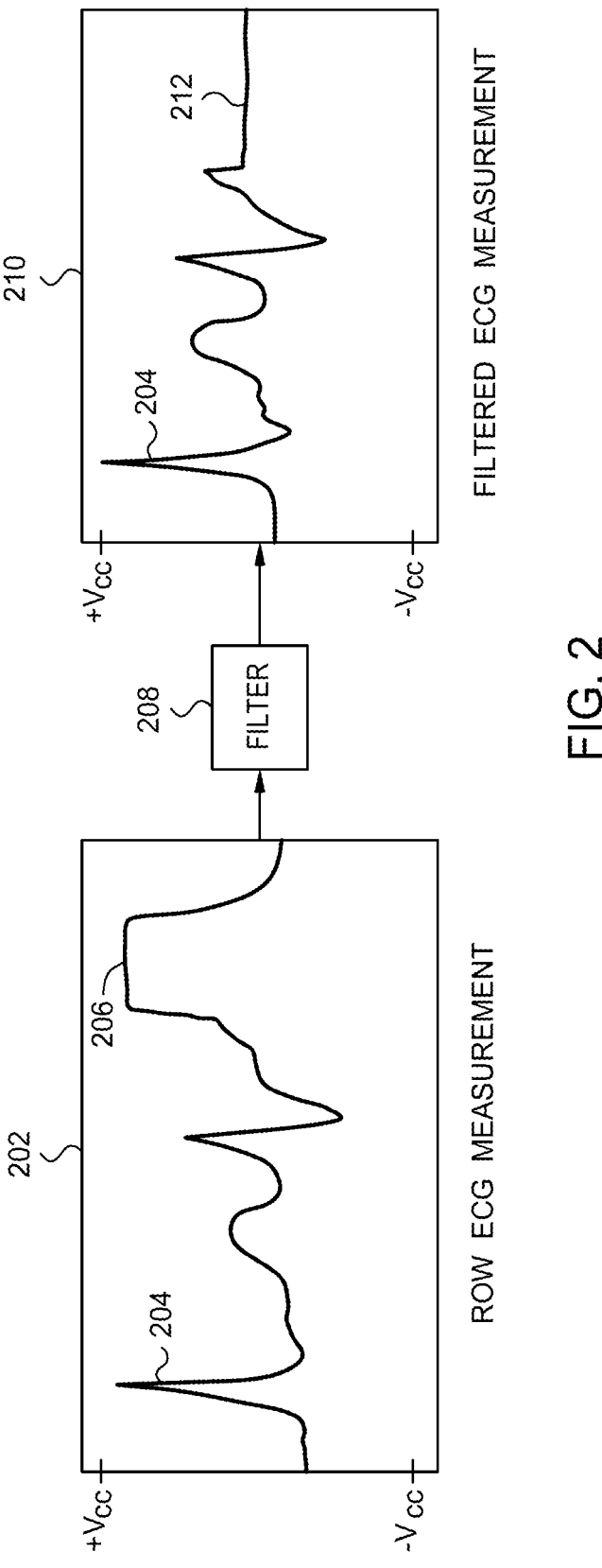
FIG. 2 illustrates an example ECG measurement in the system of FIG. 1, in accordance with various aspects of the present disclosure.

FIG. 2 illustrates an example ECG measurement in the system 100 of FIG. 1. Generally, the ECG device 104 connects to the patient 102 to measure the heartbeat of the patient 102. The ECG device 104 then produces the ECG measurement that includes an electric signal representing the heartbeat of the patient 102.

As seen in FIG. 2, the ECG device 104 produces a raw ECG measurement 202. The raw ECG measurement 202 is the electric signal directly measured from the patient 102. The electric signal has a voltage that changes according to the heartbeat of the patient 102. The voltage stays between the power supply rails (+Vcc and −Vcc) of the ECG device 104. In the example of FIG. 2, the raw ECG measurement 202 includes a voltage spike 204 and an attenuated portion 206. The voltage spike 204 and the attenuated portion 206 may be caused by movement of the patient 102 or the ECG device 104. Stated differently, the voltage spike 204 and the attenuated portion 206 may not be generated by the heartbeat of the patient 102.

The ECG device 104 may include a filter 208 that filters the raw ECG measurement 202. In some embodiments, the filter 208 may be a band pass filter that is designed to pass frequencies that are commonly seen in electric signals generated by a human heartbeat. The filter 208 filters the raw ECG measurement 202 to produce the filtered ECG measurement 210. In the example of FIG. 2, the filter 208 passes the voltage spike 204 and removes the attenuated portion 206. As a result, the filtered ECG measurement 210 includes the voltage spike 204 and a false pause region 212 that resembles a stopped heartbeat. The ECG device 104 may communicate the filtered ECG measurement 210 to the computing system 106 (shown in FIG. 1) for analysis. If the computing system 106 attempted to normalize the filtered ECG measurement 210, the voltage spike 204 would distort the normalization performed on the rest of the electric signal. Additionally, the false pause region 212 would be maintained and subsequent analysis would result in a false conclusion that the heart of the patient 102 stopped beating.

Figure 3:
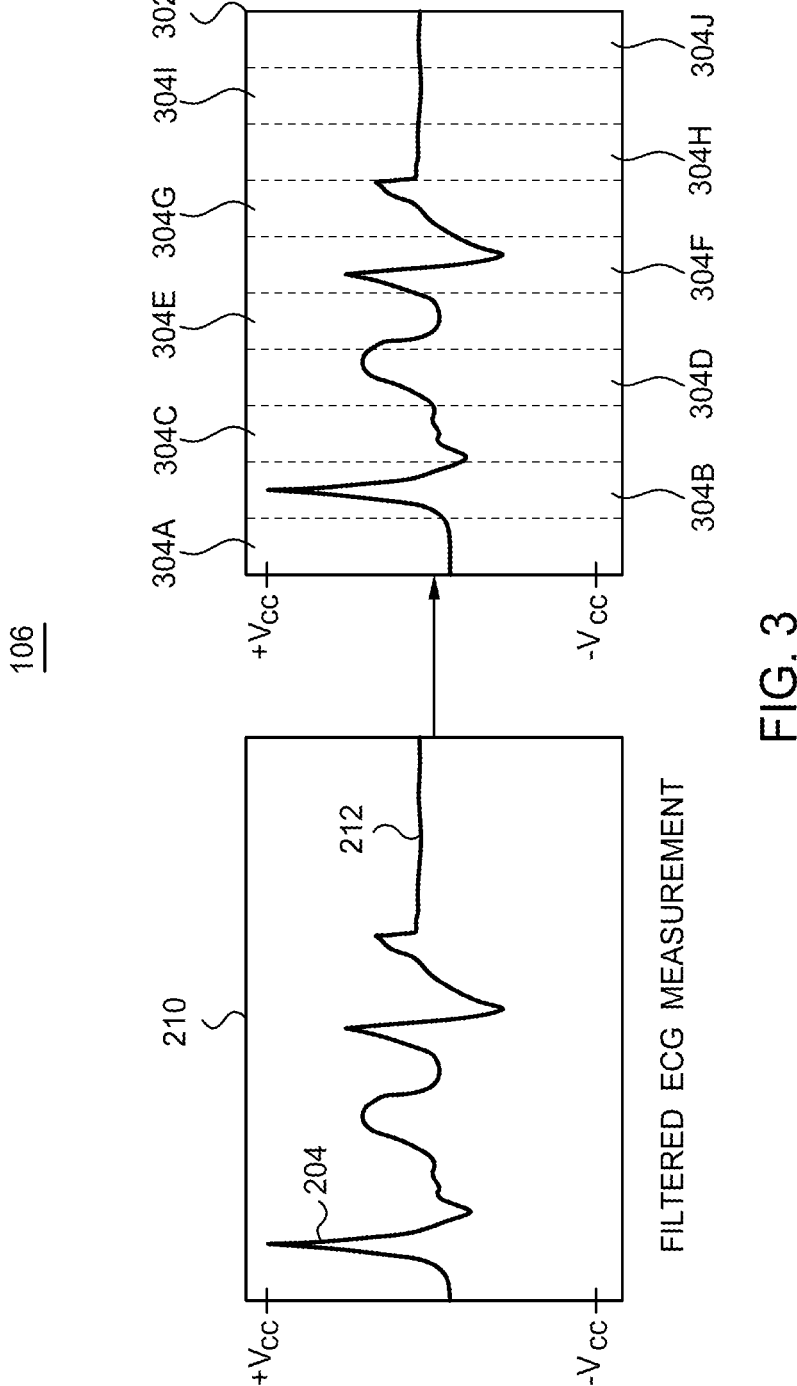
FIG. 3 illustrates an example operation of the computing system of FIG. 1, in accordance with various aspects of the present disclosure.

FIG. 3 illustrates an example operation of the computing system 106 of FIG. 1. As seen in FIG. 3, the computing system 106 divides the filtered ECG measurement 210 into multiple segments 304 to produce the segmented ECG measurement 302. Each segment 304 may be of the same duration (e.g., 125 milliseconds). The segmented ECG measurement 302 includes the segments 304A, 304B, 304C, 304D, 304E, 304F, 304G, 304H, 304I, and 304J. The voltage spike 204 is located primarily in the segment 304B. The false pause region 212 is located primarily in the segments 304H and 304I. The computing system 106 applies one or more machine learning models to the segments 304 to classify the electric signal in the segments 304 as clean, artifact, or pause.

Figure 4:
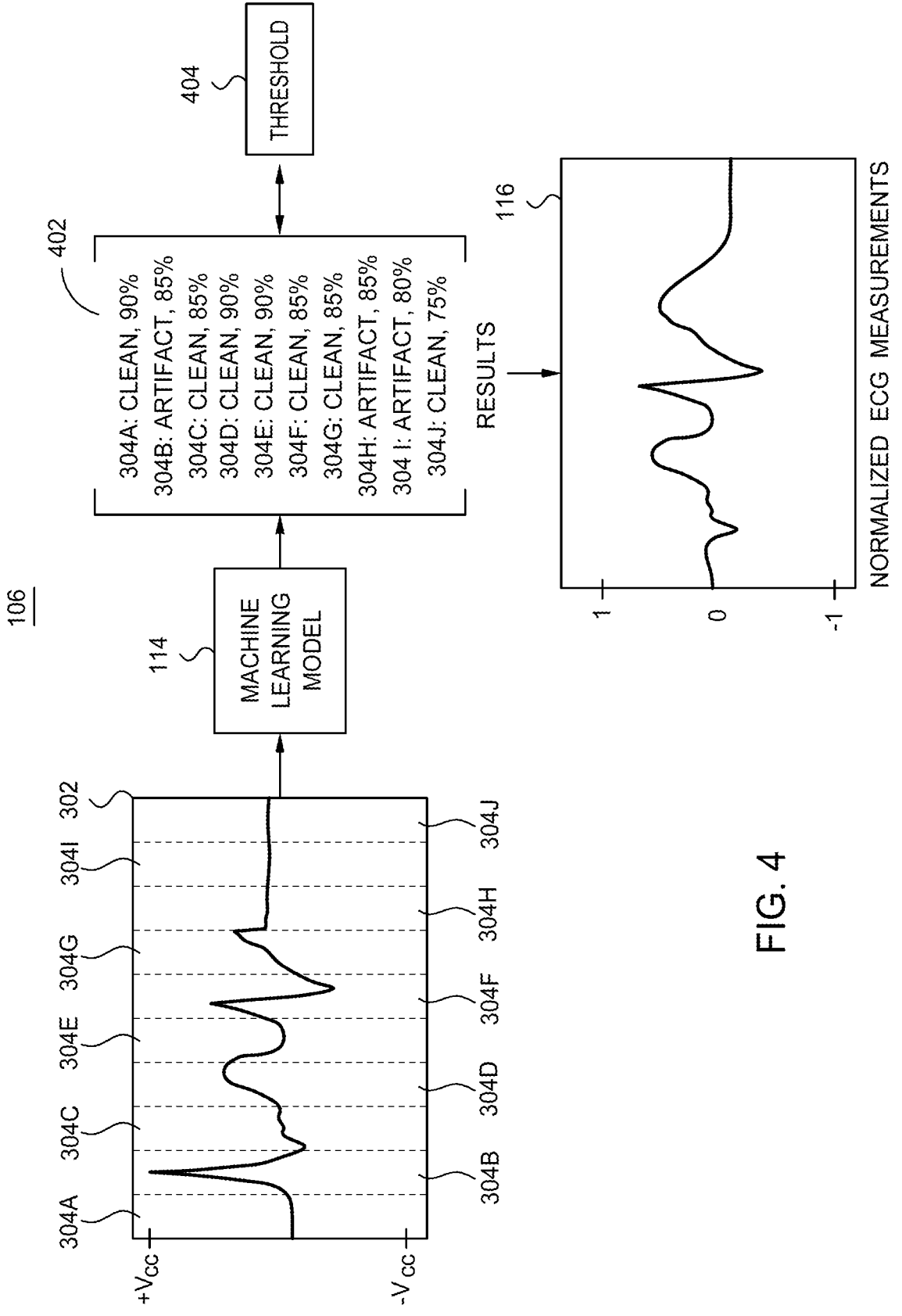
FIG. 4 illustrates an example operation of the computing system of FIG. 1, in accordance with various aspects of the present disclosure.

FIG. 4 illustrates an example operation of the computing system 106 of FIG. 1. As seen in FIG. 4, the computing system 106 applies one or more machine learning models 114 to the segmented ECG measurement 302. As discussed previously, the one or more machine learning models 114 may include neural networks and/or LSTM circuits that analyze and classify the segments 304 in the segmented ECG measurement 302. For example, a neural network may be applied to each of the segments 304 to identify features of the electric signal located in the segments 304. These features may be identified based on voltage changes in the electric signal in the segment 304. Additionally, a LSTM circuit may implement a memory component that compares the segmented ECG measurement 302 with other ECG measurements of the patient or compares a segment 304 with corresponding segments in other ECG measurements of the patient. These comparisons allow the LSTM circuit to hone the identified features in the segments 304 in the segmented ECG measurement 302. Furthermore, a neural network analyzes the honed features in the segments 304 to classify the segments 304 as clean, artifact, or pause. For example, the neural network may analyze characteristics of the features to determine whether or not those features resemble features generated by a heartbeat. If a feature resembles a feature generated by a heartbeat, the neural network may classify that segment 304 as clean. On the other hand, if a feature does not resemble a feature generated by a heartbeat, then the neural network may classify the segment 304 as an artifact. Additionally, if a feature resembles a stopped heartbeat and the neural network determines that the stoppage is real (e.g., that the stoppage spans multiple heartbeats or that the stoppage occurs during a portion of a heartbeat when a stoppage may occur), then the neural network may classify the segment 304 as a pause.

In certain embodiments, the neural network also determines a probability that its classification is correct. For example, the probability may express how closely a feature in a segment 304 resembled a feature generated by a heartbeat. If the feature closely resembled a feature generated by a heartbeat, then the neural network may classify the segment 304 as clean with a high probability of being correct. The less closely that the feature resembled a feature generated by a heartbeat, the lower the probability that the clean classification has of being correct. As another example, if a feature does not resemble a feature generated by a heartbeat, the computing system 106 may classify a segment 304 as an artifact with a high probability of being correct. The more that the feature resembled a feature generated by a heartbeat, the lower the probability that the artifact classification has of being correct.

In the example of FIG. 4, the one or more machine learning models 114 provide the results 402 after analyzing the segments 304 in the segmented ECG measurement 302. The results 402 indicate that the segment 304A has received a clean classification with a 90% probability of being correct. The segment 304B has received an artifact classification with an 85% probability of being correct. The segment 304C has received a clean classification with an 85% probability of being correct. The segment 304D has received a clean classification with a 90% probability of being correct. The segment 304E has received a clean classification with a 90% probability of being correct. The segment 304F has received a clean classification with an 85% probability of being correct. The segment 304G has received a clean classification with an 85% probability of being correct. The segment 304H has received an artifact classification with an 85% probability of being correct. The segment 304I has received an artifact classification with an 80% probability of being correct. The segment 304J has received a clean classification with a 75% probability of being correct. As seen in FIG. 4, the segments 304B, 304H, and 304I have received the artifact classification because the segment 304B includes the voltage spike and because the segments 304H and 304I include the false pause region.

In some embodiments, the computing system 106 classifies a segment 304 as an artifact using a threshold 404. For example, the computing system 106 may classify a segment 304 as an artifact and determine a probability that the classification is correct. The computing system 106 then compares that probability with the threshold 404. If the probability meets or exceeds the threshold 404 (e.g., 50%), then the computing system 106 determines that the classification is correct and classifies that segment 304 as an artifact. If the probability does not meet the threshold 404, then the computing system 106 determines that the artifact classification is incorrect and provides another classification for the segment 304. As another example, the computing system 106 may classify a segment as a pause and determine a probability that the pause classification is correct. The computing system 106 then compares that probability to the threshold 404. If the probability meets or exceeds the threshold 404 (e.g., 50%), then the computing system 106 determines that the pause classification is correct. If the probability does not meet the threshold 404, then the computing system 106 determines that the pause classification is not correct and reclassifies that segment 304 as an artifact, indicating that the pause was a false pause.

The computing system 106 normalizes the electric signal in the segmented ECG measurement 302 while taking into account the classifications provided for each segment 304 to produce the normalized ECG measurements 116. Specifically, the computing system 106 excludes the segments 304 that are classified as artifacts from the normalization. In the example of FIG. 4, the computing system 106 excludes the portions of the electric signal located in the segments 304B, 304H, and 304I from the normalization process. Stated differently, the computing system 106 does not take into account the portions of the electric signal located in the segments 304B, 304H, and 304I when normalizing the electric signal. As a result, the voltage spike and the false pause region in the segments 304B, 304H, and 304I do not affect how the electric signal is normalized. After normalizing the electric signal, the computing system 106 produces the normalized ECG measurements 116, which includes a scaled version of the electric signal with a particular average voltage (e.g., 0 volts) and standard deviation (e.g., 1 volt). In the example of FIG. 4, the normalized ECG measurements 116 include a scaled version of the electric signal with values between −1 and +1 volts.

Figure 5:
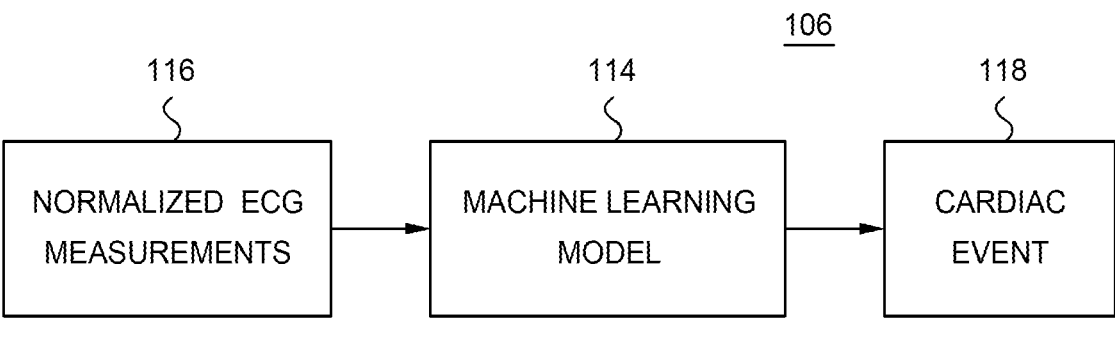
FIG. 5 illustrates an example operation of the computing system of FIG. 1, in accordance with various aspects of the present disclosure.

FIG. 5 illustrates an example operation of the computing system 106 of FIG. 1. As seen in FIG. 5, the computing system 106 applies the one or more machine learning models 114 to the normalized ECG measurements 116 to determine or predict whether a cardiac event 118 is occurring in a patient. For example, the one or more machine learning models 114 may analyze the p-waves, QRS complexes, or t-waves in the normalized ECG measurements 116 to determine whether a cardiac event 118 is occurring. As another example, the one or more machine learning models 114 may analyze the time between heartbeats as shown in the normalized ECG measurements 116 to determine whether a cardiac event 118 is occurring. As yet another example, the one or more machine learning models 114 may analyze the pauses in the normalized ECG measurements 116 to determine if a cardiac event 118 is occurring. If the computing system 106 determines that a cardiac event 118 is occurring, the computing system 106 may communicate an alert to let a monitor or administrator know that the cardiac event 118 is occurring. The monitor or administrator may prescribe proper treatment for the cardiac event 118, which improves the health of a patient.

In certain embodiments, by normalizing the ECG measurements the computing system 106 may analyze ECG measurements from different ECG devices, even though these ECG devices may have different gains, voltage ranges, or filters. Additionally, by excluding segments that are classified as artifacts from the normalization process, the computing system 106 improves the normalization process by excluding information that would distort or throw off the normalization. In this manner, the computing system 106 resolves several challenges that occur during normalization, in certain embodiments.

Figure 6:
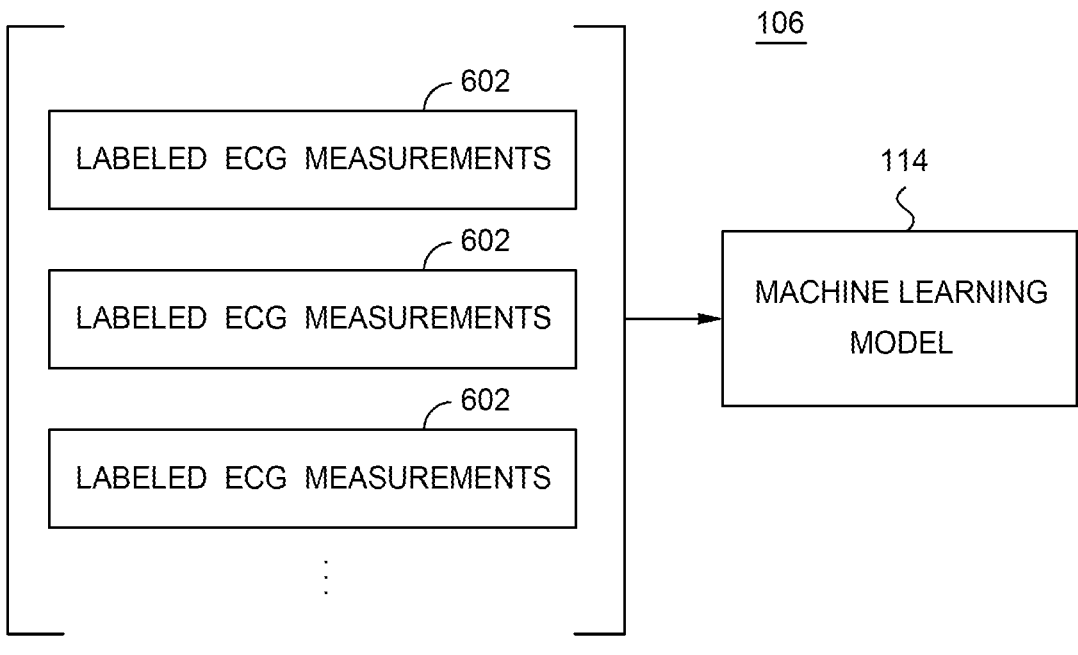
FIG. 6 illustrates an example operation of the computing system of FIG. 1, in accordance with various aspects of the present disclosure.

FIG. 6 illustrates an example operation of the computing system 106 of FIG. 1. As seen in FIG. 6, the computing system 106 trains one or more machine learning models 114 using labeled ECG measurements 602. The labeled ECG measurements 602 may include segmented ECG measurements that have been labeled with their correct classifications. The computing system 106 uses the labeled ECG measurements 602 along with the correct classifications to train the one or more machine learning models 114 to recognize clean segments, artifact segments, and pause segments. For example, the one or more machine learning models 114 may be trained to recognize what a clean segment looks like, what an artifact segment looks like, and what a pause segment looks like. After training, the computing system 106 applies the one or more machine learning models 114 to ECG measurements, and the one or more machine learning models 114 may properly classify the segments of the ECG measurements.

Figure 7:
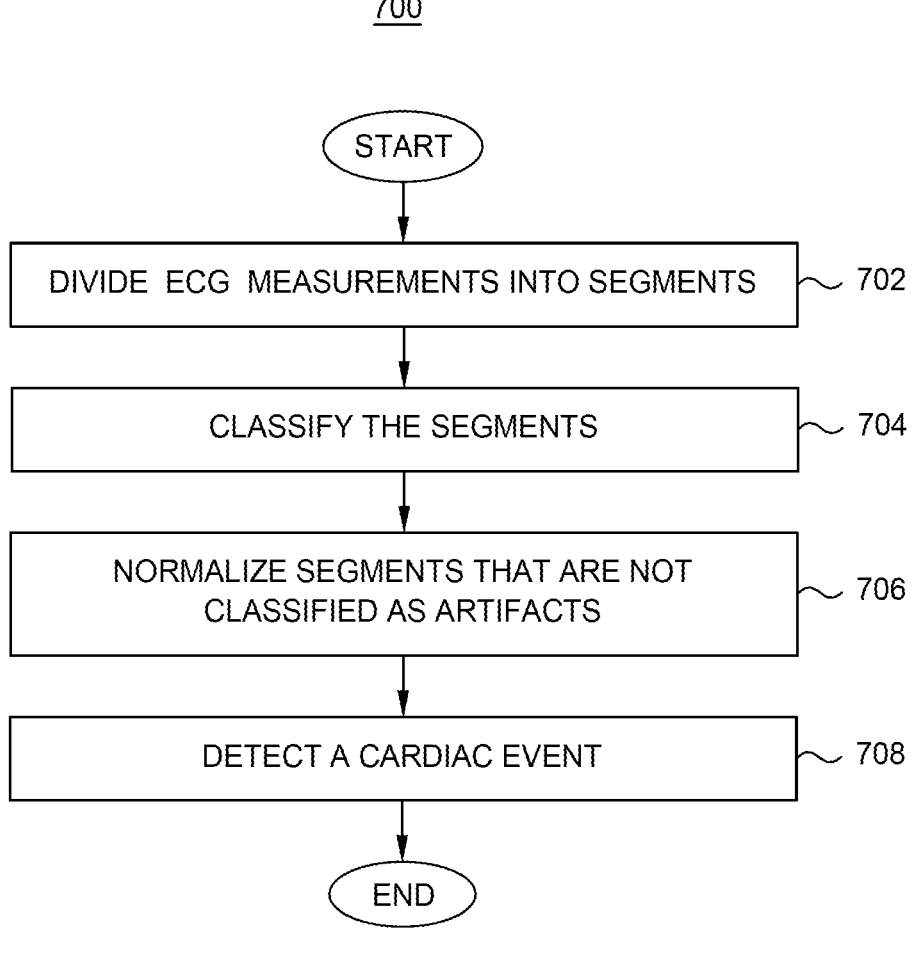
FIG. 7 is a flowchart of an example method performed in the system of FIG. 1, in accordance with various aspects of the present disclosure.

FIG. 7 is a flowchart of an example method 700 performed in the system 100 of FIG. 1. In particular embodiments, the computing system 106 performs the method 700. By performing the method 700, the computing system 106 normalizes ECG measurements. The computing system 106 excludes artifacts such as voltage spikes and false pauses from the normalization process, which improves the normalized ECG measurements and improves the accuracy of predictions made using the normalized ECG measurements.

In block 702, the computing system 106 divides an ECG measurement 210 into segments 304. Each of the segments 304 may be of the same duration (e.g., 125 milliseconds). Each of the segments 304 include a portion of an electric signal in the ECG measurement 210. The electric signal has a voltage that changes according to a heartbeat of a patient 102. Thus, the electric signal represents the heartbeat of the patient 102. The electric signal, however, may include distortions, such as voltage spikes 204 or false pause regions 212, introduced by movement of the patient or movement of an ECG device 104 connected to the patient 102. These distortions may result in inaccuracies if the ECG measurement 210 were to be normalized.

In block 704, the computing system 106 classifies the segments 304. The computing system 106 applies one or more machine learning models 114 to the electric signal in the segments 304 to classify the electric signal in those segments 304 as clean, artifact, or pause. The clean classification indicates that the portion of the electric signal in a segment 304 is generated by a heartbeat. The artifact classification indicates that a portion of the electric signal in a segment 304 is not generated by a heartbeat. The pause classification indicates that a portion of the electric signal in a segment 304 is generated by a stopped heartbeat. In some embodiments, the computing system 106 applies a neural network to the segments 304 to identify features in the electric signal in the segments 304. For example, the neural network may identify voltage changes in the electric signal in the segments 304 to identify the features. The machine learning model 114 then applies a LSTM circuit that implements a memory component to compare the segments 304 to segments in other ECG measurements generated by other heartbeats. The LSTM circuit hones the identified features based on the comparisons with other heartbeats. The computing system 106 then applies a neural network to the honed features to classify the segments 304 that contain the honed features. For example, the neural network may analyze a honed feature to determine whether the honed feature was generated by a heartbeat or not. In some embodiments, the neural network classifies the segment 304 and produces a probability that the classification is correct. The computing system 106 then compares that probability to a threshold 404. If the probability does not meet the threshold 404, the computing system 106 may change the classification (e.g., from clean or pause to artifact).

In block 706, the computing system 106 normalizes segments 304 that are not classified as artifacts. Specifically, the computing system 106 normalizes the portions of the electric signal that are located in segments 304 that are not classified as artifacts. During normalization, the computing system 106 scales the electric signal such that the normalized electric signal has a particular average voltage (e.g., zero volts) and a certain standard deviation (e.g., one volt). By excluding the portions of the electric signal that are classified as artifacts from the normalization, the computing system 106 prevents the artifacts, such as voltage spikes or false pauses, from distorting the normalized ECG signal.

In block 708, the computing system 106 detects a cardiac event 118 based on the normalized electric signal. For example, the computing system 106 may apply a machine learning model 114 to the normalized ECG signal to determine whether a cardiac event 118 is occurring in a patient. The machine learning model 114 may analyze characteristics of the p-waves, QRS complexes, and t-waves in the normalized signal to determine if a cardiac event 118 is occurring. As another example, the machine learning model 114 may analyze a time between heartbeats indicated by the normalized ECG signal to determine whether a cardiac event 118 is occurring. In some embodiments, if the computing system 106 detects a cardiac event 118, the computing system 106 communicates an alert to let a monitor or an administrator know of the cardiac event 118. The monitor or administrator may then prescribe the proper treatment for the cardiac event 118, which improves the health of the patient 102.

In summary, a computing system 106 uses machine learning to normalize ECG wave signals. The computing system 106 applies one or more machine learning models 114 to an ECG wave signal to label portions of the ECG wave signal as "clean" (indicating that the portion represents a heartbeat), "artifact" (indicating that the portion does not represent a heartbeat), or "pause" (indicating that the portion represents a stopped heartbeat). The computing system 106 then normalizes the ECG wave signal but excludes the portions labeled "artifact" from the normalization. As a result, the normalization is not performed on artifacts (e.g., voltage spikes and false pauses) that negatively impact or degrade the normalization. The computing system 106 applies the one or more machine learning models 114 to the normalized ECG wave signal to detect cardiac events 118. In certain embodiments, the normalized ECG wave signal produces a more accurate detection or prediction of cardiac events 118, which improves the health of a patient 102.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The above detailed description is intended to be illustrative, and not restrictive. The scope of the disclosure should, therefore, be determined with references to the appended claims, along with the full scope of equivalents to which such claims are entitled.

I claim:

1. A method comprising:

training a machine learning model using labeled electrocardiogram measurements, wherein the labeled electrocardiogram measurements comprise labeled segments, and wherein the labeled segments comprise a segment labeled as an artifact;

classifying, using the machine learning model, a portion of an electrocardiogram measurement as an artifact, wherein the classifying the portion as the artifact comprises:

classifying the portion as a pause indicating that a heart stopped, determining a probability that classifying the portion as the pause is correct, and classifying the portion as the artifact in response to determining that the probability does not meet a threshold;

normalizing the electrocardiogram measurement except the portion of the electrocardiogram measurement classified as the artifact; and detecting a cardiac event from the normalized electrocardiogram measurement.

2. The method of claim 1, wherein the electrocardiogram measurement classified as the artifact is a bandpass filtered electrocardiogram measurement.

* * * * *